United States Patent
Bianchi et al.

(10) Patent No.: US 12,083,070 B2
(45) Date of Patent: *Sep. 10, 2024

(54) CONTAINER FOR STORING A DRUG SUCH AS INSULIN

(71) Applicant: Debiotech S.A., Lausanne (CH)

(72) Inventors: François Bianchi, Martigny (CH); Gian-Luca Lettieri, Neuchâtel (CH); Stephan Proennecke, Gex (FR)

(73) Assignee: DEBIOTECH S.A., Lausanne (CH)

( * ) Notice: Subject to any disclaimer, the term of this patent is extended or adjusted under 35 U.S.C. 154(b) by 77 days.

This patent is subject to a terminal disclaimer.

(21) Appl. No.: 17/577,071

(22) Filed: Jan. 17, 2022

(65) Prior Publication Data

US 2022/0175616 A1  Jun. 9, 2022

Related U.S. Application Data

(63) Continuation of application No. 14/236,716, filed as application No. PCT/IB2012/053827 on Jul. 26, 2012, now Pat. No. 11,266,567.

(30) Foreign Application Priority Data

Aug. 10, 2011 (EP) ..................... 11177173

(51) Int. Cl.
*A61J 1/14* (2023.01)
*A61M 5/142* (2006.01)

(52) U.S. Cl.
CPC ............ *A61J 1/14* (2013.01); *A61M 5/14248* (2013.01); *A61M 2205/02* (2013.01); *A61M 2205/0216* (2013.01)

(58) Field of Classification Search
CPC .......... A61M 5/14248; A61M 2205/02; A61M 2205/0216
See application file for complete search history.

(56) References Cited

U.S. PATENT DOCUMENTS

| | | |
|---|---|---|
| 2,631,847 A | 3/1953 | Hornberger |
| 3,771,694 A | 11/1973 | Kaminski |
| 4,226,952 A | 10/1980 | Halasa |
| 4,498,843 A | 2/1985 | Schneider et al. |
| 4,544,369 A | 10/1985 | Skakoon et al. |
| 4,657,486 A | 4/1987 | Stempfle et al. |
| 5,520,975 A | 5/1996 | Inoue et al. |

(Continued)

FOREIGN PATENT DOCUMENTS

| | | |
|---|---|---|
| CN | 1091710 A | 9/1994 |
| CN | 102202708 A | 9/2011 |

(Continued)

OTHER PUBLICATIONS (TOPAS)—Advanced Polymers Announces Developmental Grades of TOPAS Cyclic Olefin Copolymer (COC) Elastomer—Sep. 30, 2010 (Year: 2010).*

(Continued)

*Primary Examiner* — James D Ponton
(74) *Attorney, Agent, or Firm* — NIXON & VANDERHYE

(57) ABSTRACT

A polymeric container for storing a drug such as insulin which comprises a hard shell (2) and a flexible film (1), wherein both elements are made from the same material.

25 Claims, 12 Drawing Sheets

(56) References Cited

U.S. PATENT DOCUMENTS

| | | |
|---|---|---|
| 5,938,640 A | 8/1999 | Maget |
| 5,957,895 A | 9/1999 | Sage et al. |
| 6,485,461 B1 | 11/2002 | Mason et al. |
| 6,589,198 B1 | 7/2003 | Soltanpour et al. |
| 6,589,229 B1 | 7/2003 | Connelly et al. |
| 6,723,072 B2 | 4/2004 | Flaherty et al. |
| 6,740,059 B2 | 5/2004 | Flaherty |
| 7,935,104 B2 | 5/2011 | Yodfat et al. |
| 8,298,183 B2 | 10/2012 | Menot et al. |
| 9,452,593 B2 | 9/2016 | Tatarka et al. |
| 2003/0170410 A1 | 9/2003 | Buch-Rasmussen et al. |
| 2003/0208184 A1 | 11/2003 | Burke |
| 2003/0220605 A1* | 11/2003 | Bowman, Jr. ......... A61M 5/145 264/109 |
| 2004/0013575 A1 | 1/2004 | Stevens |
| 2004/0115068 A1* | 6/2004 | Hansen ................ F04B 19/24 417/379 |
| 2004/0138612 A1* | 7/2004 | Shermer ........... A61M 5/14248 604/93.01 |
| 2006/0054557 A1 | 3/2006 | Hori |
| 2006/0134358 A1* | 6/2006 | Madsen ................ B32B 1/08 428/35.2 |
| 2007/0043335 A1 | 2/2007 | Olsen et al. |
| 2009/0105684 A1 | 4/2009 | Balteau et al. |
| 2009/0247982 A1* | 10/2009 | Krulevitch ........ A61M 5/14224 604/151 |
| 2009/0259198 A1 | 10/2009 | Chong et al. |
| 2009/0311133 A1* | 12/2009 | Pang ................... A61M 5/142 216/33 |
| 2010/0228196 A1 | 9/2010 | Wyss |
| 2010/0294693 A1 | 11/2010 | Lynn |
| 2011/0144585 A1 | 6/2011 | Bianchi et al. |
| 2011/0172639 A1 | 7/2011 | Moga et al. |
| 2013/0253439 A1 | 9/2013 | Wyss et al. |

FOREIGN PATENT DOCUMENTS

| | | |
|---|---|---|
| EP | 1839695 | 10/2007 |
| EP | 11 177 173.9 | 8/2011 |
| EP | 2455126 A1 | 5/2012 |
| EP | 2741726 B1 | 7/2017 |
| EP | 2741726 B2 | 8/2020 |
| JP | 2006501043 | 1/2006 |
| WO | WO 9827925 | 7/1998 |
| WO | WO 01/94784 A1 | 12/2001 |
| WO | WO 2004032990 | 4/2004 |
| WO | WO 2010023567 | 3/2010 |
| WO | WO 2011014839 | 2/2011 |
| WO | WO 2011129869 | 10/2011 |
| WO | WO 20120065780 | 5/2012 |

OTHER PUBLICATIONS

Affidavit of Paul D. Talarka, daled Jul. 1, 2019, 28 pages.
Affidavit of Randy Jester, daled Jul. 2, 2019, 28 pages.
Chinese Office Action dated Jul. 16, 2019 for Divisional Application No. CN 201710111538.3.
Communication pursuant to Article 94(3) EPC dated Oct. 23, 2020, issued in European Application No. 17181711.7.
Communication pursuant to Article 94(3) EPC dated Sep. 7, 2015, issued in European Patent Application No. 12 758 635.2.
International Preliminary Report on Patentability (IPRP) Chapter I, issued Feb. 11, 2014 for applicant's PCT/IB2012/053827 dated Jul. 26, 2012.
International Search Report for PCT/IB2012/053827 mailed Nov. 13, 2012.
Jester, Randy; Cyclic Olefin Copolymer Enhances Polyolefin Blends for Film Packaging; from Plastics Technology May 2011; screenshotted Jun. 8, 2011 ; https ://web .archive .org/web/20110608030220/ https ://www .ptonl ine .corn/articles/.
Notice of Reasons for Rejection dated Jun. 7, 2016, issued in Japanese Patent Application No. 2014-524464, and English translation.
OEB 94.3 dated Feb. 28, 2020 for application EP 17181711.7.
Opposition against European Paient No. 27 41726B 1, Proprietor: Debiolech S.A., Opponent: TOPAS Advanced Polymers GmbH, dated Jul. 10, 2019, 19 pages.
Opposition Against European Patent No. 2 741 726 B1 dated Feb. 16, 2018, 55 pages.
Opposition Decision dated Dec. 5, 2019, issued in European Application No. 12 758 635.2.
Opposition Form EPA 2300 against European Patent No. 2 741 726 B1 dated Feb. 16, 2018, 5 pages.
The Second Office Action dated Oct. 28, 2015, issued in Chinese Patent Application No. 201280038191X, and English translation.
TOPAS Advanced Polymers, Inc.—Modified Cyclic Olefin Copolymers as New Cost and . . . .
TOPAS Elastomer E-140 Now avalaible.
Written Opinion of the International Searching Authority mailed Nov. 13, 2012.
TOPAS Advanced Polymers Announces Developmental Grades of TOPAS® Cyclic Olefin Copolymer (COC) Elastomer.
Compatibility of Insulin Lispro, Aspart, and Glulisine with the Solo™ MicroPump, a Novel Miniature Insulin Pump.

\* cited by examiner

CONTAINER FOR STORING A DRUG SUCH AS INSULIN

CROSS-REFERENCE TO RELATED APPLICATIONS

The present application is a continuation application (CONT) of U.S. Ser. No. 14/236,716, now U.S. Pat. No. 11,266,567, that was filed on Feb. 3, 2014, which is a United States national stage application of International patent application PCT/IB2012/053827 that was filed on Jul. 26, 2012, which designated the United States, and claims foreign priority to European patent application EP 11177173.9, filed on Aug. 10, 2011, the entire contents of all three (3) documents being herewith incorporated by reference.

FIELD OF INVENTION

The invention relates to medical containers, in particular containers for storing insulin.

STATE OF THE ART

Several insulin infusion devices are currently available on the market. The first generation of disposable syringe-type containers and tubes are described, for example, in U.S. Pat. Nos. 2,631,847, 3,771,694, 4,657,486, and 4,544,369. Generally, the containers of these devices are symmetrical, round, and tubular-shaped, and have rigid walls to enable smooth movement of the pump piston (plunger) and to maintain proper sealing.

The relatively bulky devices have to be carried in a patient's pocket or be attached to the patient's belt. Consequently, the fluid delivery tube is long, usually longer than 60 cm, to enable needle insertion in remote sites of the body. These uncomfortable bulky fluid delivery devices with long tubing are not popular with the majority of diabetic insulin users, because these devices interfere with regular activities, such as sleeping and exercising. Furthermore, the effect of the image projected on a teenagers' body is unacceptable among teenagers.

To avoid tubing limitations, a second generation of pumps has been developed. These pumps include a housing having a bottom surface adapted for attachment to the user's skin, a container disposed within the housing, and an injection needle adapted to be in fluid communication with the container. These skin adhered devices typically are discarded of every 2-3 days, similarly to the infusion sets employed with the pumps of the first generation. Such second-generation devices are described, for example, in U.S. Pat. Nos. 4,498,843, 5,957,895, 6,589,229, and 6,740,059. Other configurations of skin-secured pumps are disclosed, for example, in U.S. Pat. Nos. 6,723,072 and 6,485,461. The containers of such devices, like the containers used in 1st generation pumps, are usually tubular and syringe like, thus requiring a relatively large occupying space and a thick housing.

To address the volume and cost constraints, a $3^{rd}$ generation skin-secured pump was proposed as described, for example, in U.S. Pat. No. 7,935,104. In such as a dispensing patch unit-the dispensing patch unit includes two parts, a disposable part and a reusable part. The reusable part generally includes electronic components and the metering portion. The disposable part generally includes an inlet port to fill the container for therapeutic fluid, a filter protecting a short drug delivery as well as the pumping mechanism and an exit port. After connection of the reusable and disposable parts, the assembled device has a very thin dimension, rendering the whole device inexpensive, light and discrete.

General Description of the Invention

The invention concerns a polymeric container for storing a drug, e.g. insulin, which comprises a hard shell and a flexible film, wherein both elements are made from the same material.

For the present invention, a same material is a material which is made from the same chemical entity, the same polymer or monomer. Furthermore, even if the process used to make said both elements is different, said elements have at least one same feature.

As a non-limiting example, if a same monomer forms after polymerization a series of chains, it may present different mechanical properties that the same monomer polymerized forming a network. We consider in this invention these two materials as the same material.

Advantageously the hard shell is made of a single layer.

The rigidity of the hard shell and the flexibility of the film may be obtained in different ways, some being disclosed in the present document. For instance the flexible film may be manufactured according to a process which consists in the preparation of a blend of a rigid polymeric material with an elastomeric formulation of the same material.

The container according to the invention may advantageously be used as a therapeutic fluid container combination with a portable skin patch infusion device for diabetes CSII therapy. In one embodiment, the container includes a hard shell on which there is a thermoformed flexible film that fits the hard shell closely, minimizing dead volume and air bubble during the filling procedure performed by the patient. Preferably the hard shell and the flexible film are both made of cyclic olefin polymer (COC) and ensure the integrity of the drug solution for the intended use.

One original feature of this container compared to similar existing technology consists in the fact that the flexible film is composed of a material made from the same polymer than the hard shell. In a preferred embodiment, for the film, a COC elastomer is used as a modifier for COC to obtain a flexible film with greater toughness and enhanced sustainability. Film strength is greatly improved in COC formulations containing 25% or less of the COC elastomer.

In another embodiment the container according to the invention is transparent.

The container preferably has an inlet port that enables filling and maintains sealing and can be filled by a syringe and an outlet port protected by a filter that is connected to the delivery fluid in a way that prevents entrapment of air bubbles.

The material of the container may be made from a material with a low temperature melting point, thus enabling heat welding and it may resist high temperature(s) including welding temperature(s). The container may be sufficiently moisture proof, preservative (e.g. phenol, m-cresol) proof to enable for storage of a medicament containing water and preservatives (e.g., phenol, m-cresol), without significant changes in potency of medicament for the entire usage duration (e.g., 6 to 12 days). The container's geometrical structure may enable for optimal filling of the fluid and complete or almost complete emptying with minimal if any residual volume. The single material semi-flexible container is provided that holds fluids and maintains the chemical stability of a drug and/or preservatives held in the container, and also avoids leachable material. Additionally, the container's thin wall is adapted to serve as a barrier against fluid vapor and is chemically inert to the absorption of fluid constituents (e.g. water, m-cresol, phenol), as indicated by the wall material's relatively low Moisture vapour Transmission Rate (MVTR). Thus, the thickness of the container walls should be sufficient to enable maximum of 1.5% per day loss of fluid.

For example, flexible film may be shaped by thermo forming and then welded together with the hard shell, which is obtained by injection molding, containing the inlet and outlet port assemblies without gluing. Said film may be shaped in a way as to closely fit the shape of the hard shell (2) on which contact may be made. The flexible membrane is collapsed on the hard shell during the fabrication to avoid trapping of air bubbles during the filling. Moreover the collapsible container can be sterilized, for example, by gamma irradiation and can be manufactured by a production method that maintains its biocompatibility and that avoids use of adhesive materials such as glue. The container may be welded and the inlet and outlet ports may be connected by pressure to a pumping mechanism.

LIST OF FIGURES

List of Elements:
(1) flexible film,
(2) hard shell,
(3) filter,
(4) inlet port,
(5) outlet port,
(6) bottom shell,
(7) pumping mechanism

DETAILED DESCRIPTION OF THE INVENTION

The invention will be better understood with the following non-exclusive examples, some of them being illustrated.

The present invention preferably proposes the use of cyclic olefin copolymers (COC) as special class of polymeric materials with property profiles which can be varied over a wide range during polymerisation as the base material to produce a transparent, semi-flexible, watertight container made of a single layer soft film thermo-formed and collapsed onto a hard shell, made with same material, which should include one or more of the following properties:

1. Compatible with the active ingredient of the drug (insulin)
2. Impervious or substantially impervious to fluid loss, e.g., water and preservatives, e.g., m-cresol, present in the contained fluid;
3. Suitable MVTR and thickness;
4. Mechanical properties enabling flexibility and collapsibility.
5. Sterilisable (e.g. gamma irradiation, steam, ethylene oxide);
6. Non leachable or substantially non leachable;
7. Weld capable.

The high transparency of Topas COC in the visible and near ultraviolet regions coupled with a refractive index of 1.53 (Topas 5013) makes the polymer suitable for application where transparency is necessary. Topas COC exhibits a unique combination of properties—glass-clear transparency, superior water vapour barrier, low water absorption and good chemical resistance to aqueous media, acids and alkalis and to polar organics. Thus, together with their excellent biocompatibility, these materials are of particular interest for primary packaging of pharmaceuticals, medical devices and diagnostic disposables.

Container Design

A possible design of the container is described in the figures. The container includes inlet port for the filling as septum, a filter to protect the downstream fluidic path as well as the pumping mechanism which is a MEMS in this case, and the cannula connector exit port. The flexible film is also protected from mechanical contact by a bottom shell.

Figure 1:
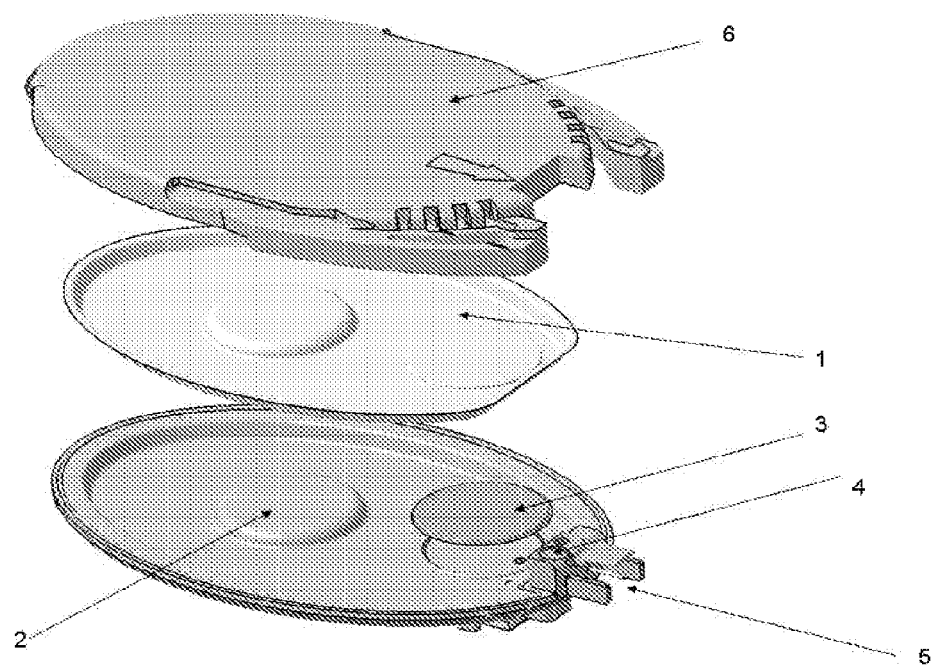
FIG. 1 is an exploded view of a container.

FIG. 1 is an exploded view of a container showing the main components (1) flexible film, (2) hard shell, (3) filter, (4) inlet port, (5) outlet port and (6) bottom shell.

Figure 2:
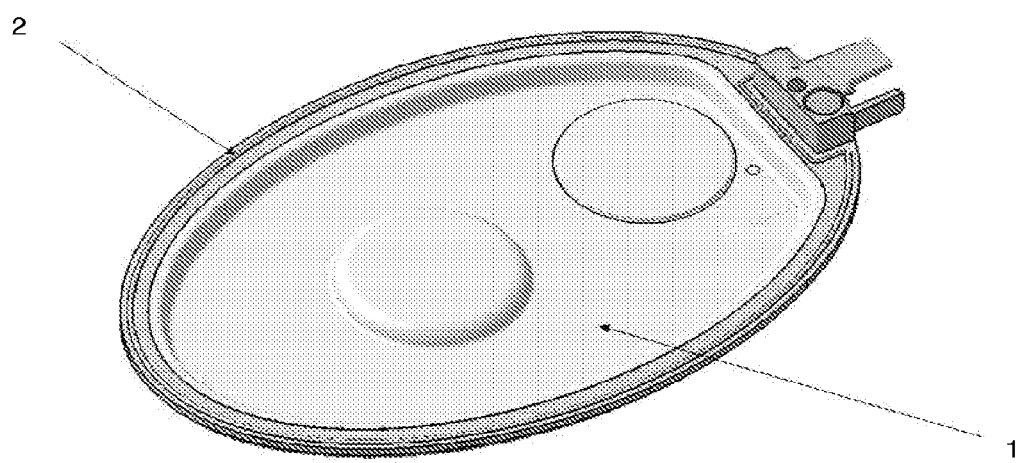
FIG. 2 shows the flexible film (1) collapsed onto the hard shell (2).

FIG. 2 shows the flexible film (1) collapsed onto the hard shell (2).

Figure 3:
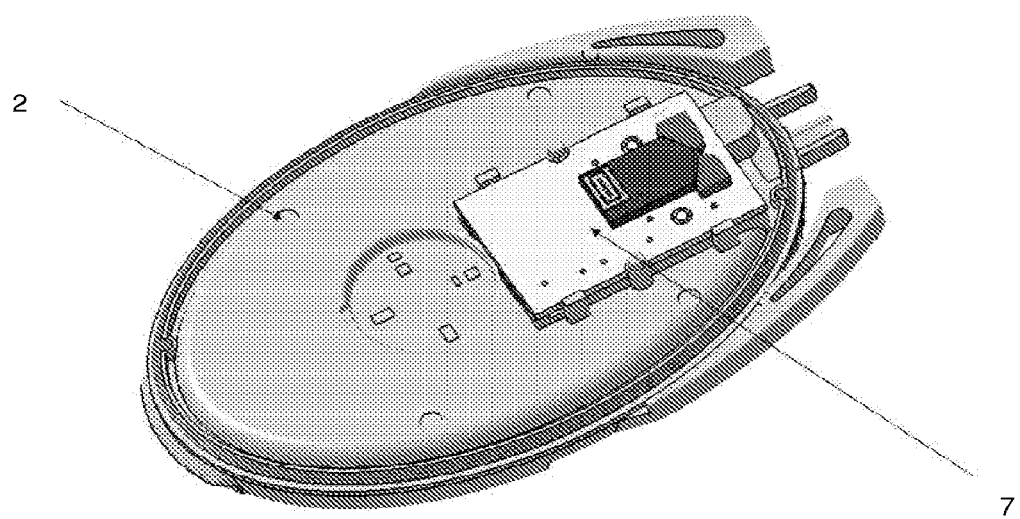
FIG. 3 is a bottom view of the hard shell (2) interfaced with pumping mechanism (7).

FIG. 3 is a bottom view of the hard shell (2) interfaced with pumping mechanism (7) forming the downstream fluidic path protected by the filter (3) and connected to exit port (5).

In one embodiment, the flexible film (1) is enclosed into an additional hard shell, said additional hard shell containing openings to guarantee pressure equilibrium between the inside of said additional hard shell and the outside.

Drug Compatibility and Integrity

The container should demonstrate good compatibility of insulin solutions (Aspart) for a period of 12 days, which represents a safety margin of two compared to the labelled intended use (6 days). The compatibility of the drug will be assessed through stability and appearance.

Figure 4:
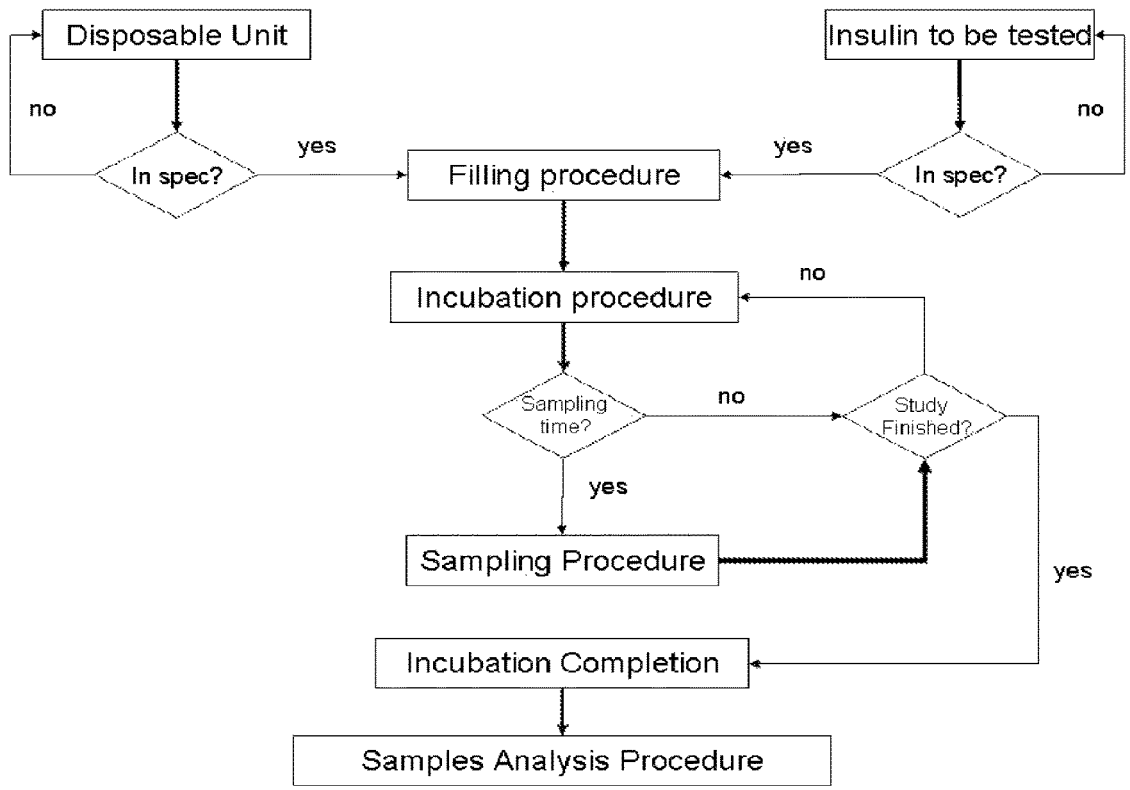
FIG. 4 represents the procedure of testing is described by the flowchart

The procedure of testing is described by the flowchart represented on FIG. 4.

The target stability of this study being of 6 days, for safety reasons the study has been run for 13 days to simulate a worst-case scenario at 37° C. For the insulin, two sampling points had been selected, after 6 and 13 days of incubation.

The acceptance criteria and the reference for each test to demonstrate drug integrity are listed in Table 1. The methods of analysis and data treatment are performed using an external protocol and a validated method.

TABLE 1

Acceptance criteria for tests conducted obtained from the British Pharmacopoeia 2009 (BP) and from insulin manufacturer certificate of analysis (COA).

| Study | Acceptance criteria | Unit |
|---|---|---|
| Appearance* | Clear, colorless liquid, no particles | N/A |
| Insulin content * | 90-110 | [%] |
| m-cresol content* | 90-110 | [%] |
| Phenol content* | 90-110 | [%] |
| HMWP content* | ≤1.5 | [%] |
| B3Asp + A21Asp + B3isoAsp content* | ≤5 | [%] |
| B28isoAsp content* | ≤2.5 | [%] |
| Other impurities* | ≤3.5 | [%] |

Figure 5:
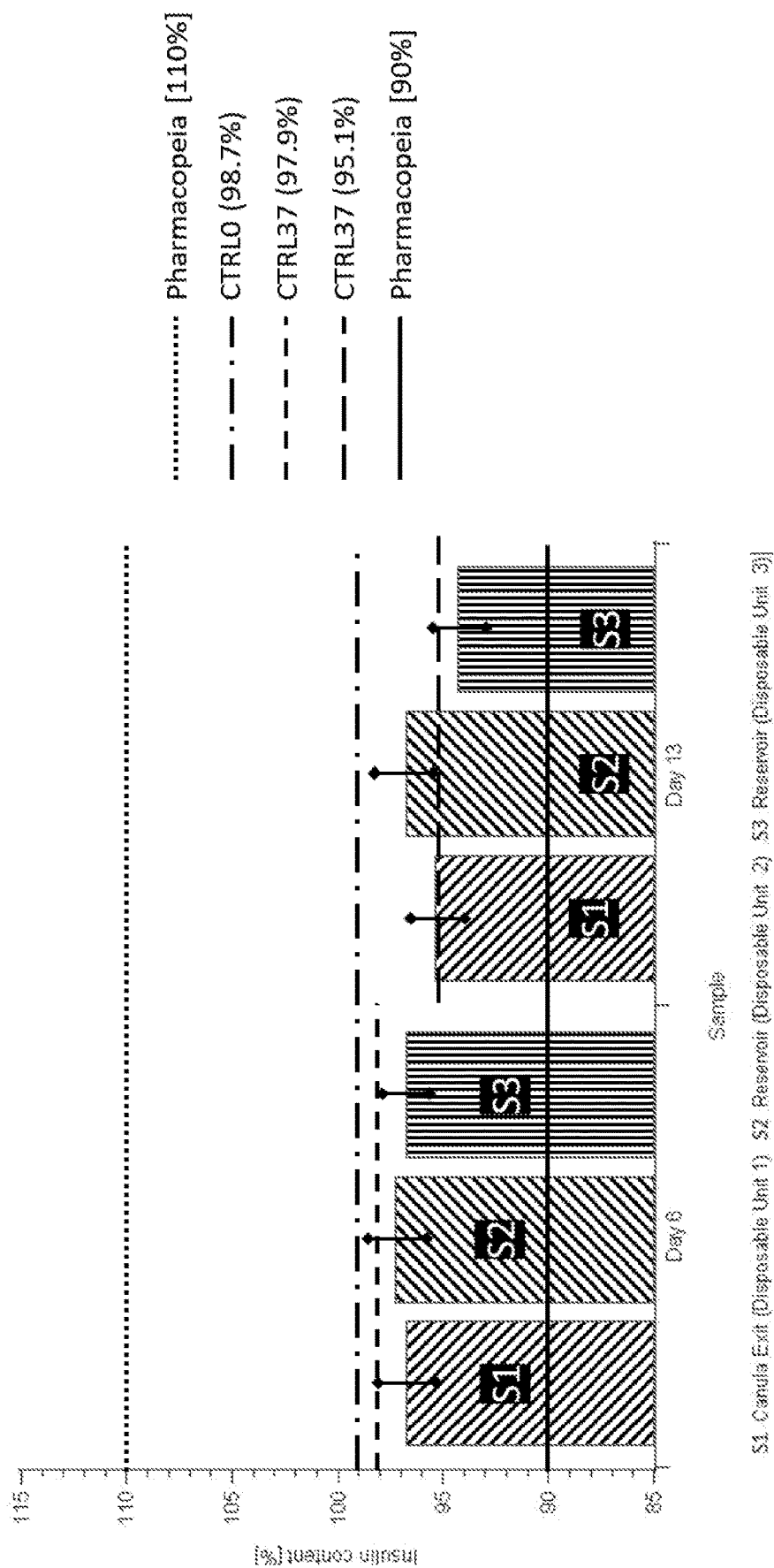
FIG. 5 shows the Insulin potency of insulin Aspart

The results regarding insulin content are presented in FIG. 5, which more precisely shows the Insulin potency of insulin Aspart. The results for three Disposable Unit samples are presented as relative percentages to a standard solution; the error bar is RSD (1.4%) of the HPLC analysis. The "Pharmacopeia" lines are the limit acceptance criteria (90-110%), another line is the Control T at 5° C. (CTRL0 bulk solutions of the insulin vial) and another line is Control T at 37° C. (CTRL37 bulk solutions of the insulin vial) where insulin was exposed to thermal stresses in its original packaging.

Insulin analog solution contains antimicrobial preservatives: Aspart solution-m-cresol (1.72 mg/mL) and phenol (1.5 mg/mL) that should be maintained in at a sufficient level to ensure antimicrobial efficiency as mentioned in the USP.

Figure 6:
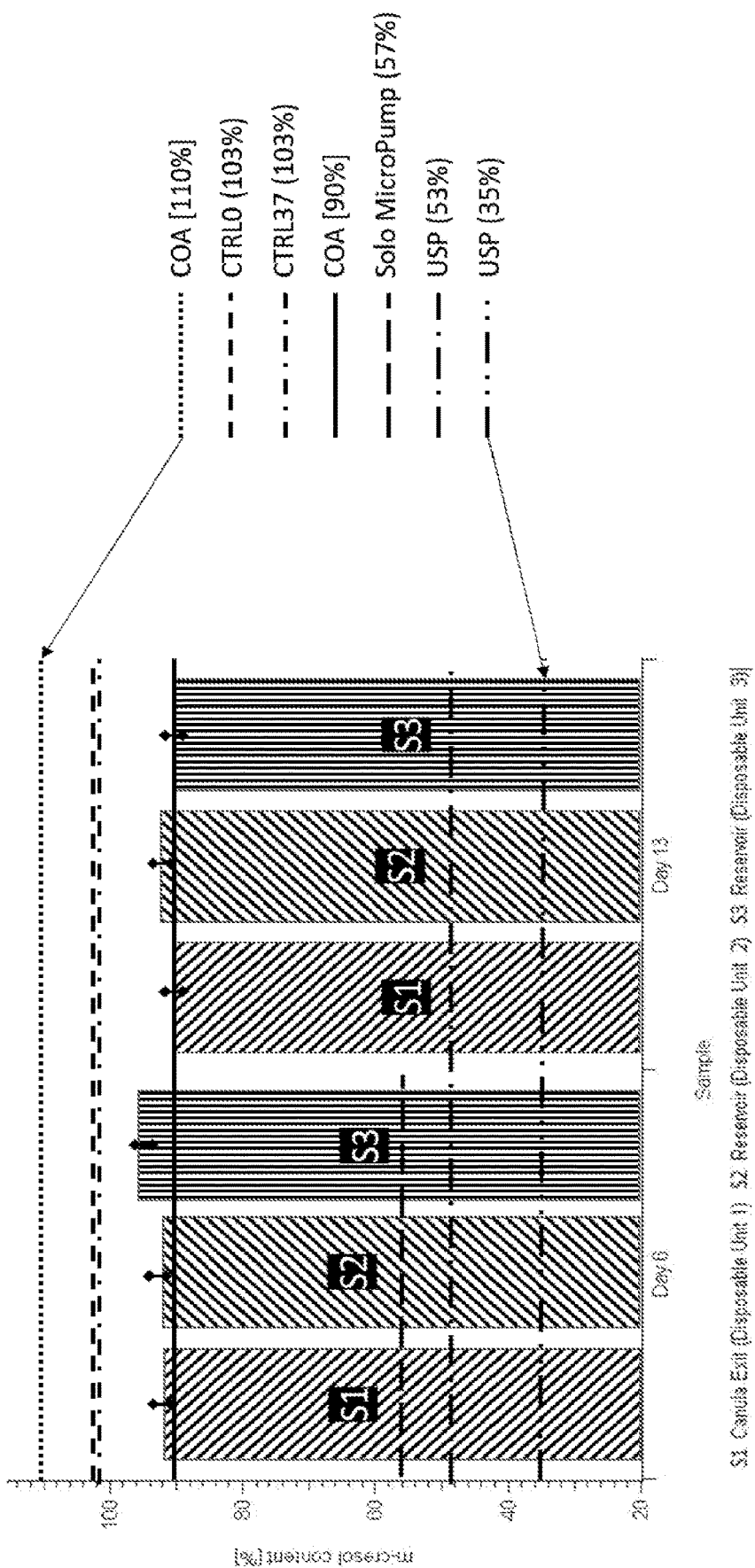
FIG. 6 shows preservative levels of m-cresol in insulin Aspart.

FIG. 6 shows preservative levels of m-cresol in insulin Aspart. The results for three Disposable Unit samples are presented as relative percentages to a standard solution; the error bar is RSD (0.8%) of the HPLC analysis. The COA lines are the limit acceptance criteria (90-110%), another line is the Control Tat 5° C. (CTRL0 bulk solutions of the insulin vial) and another line is Control T at 37° C. (CTRL37 bulk solutions of the insulin vial) where insulin was exposed to thermal stresses in its original packaging. The "Solo Micropump" dashed line represents the m-cresol level at the Solo MicroPump exit after 6 days of incubation in similar experimental conditions and the "USP" dash lines represent the m-cresol effectiveness level according to USP standard.

Figure 7:
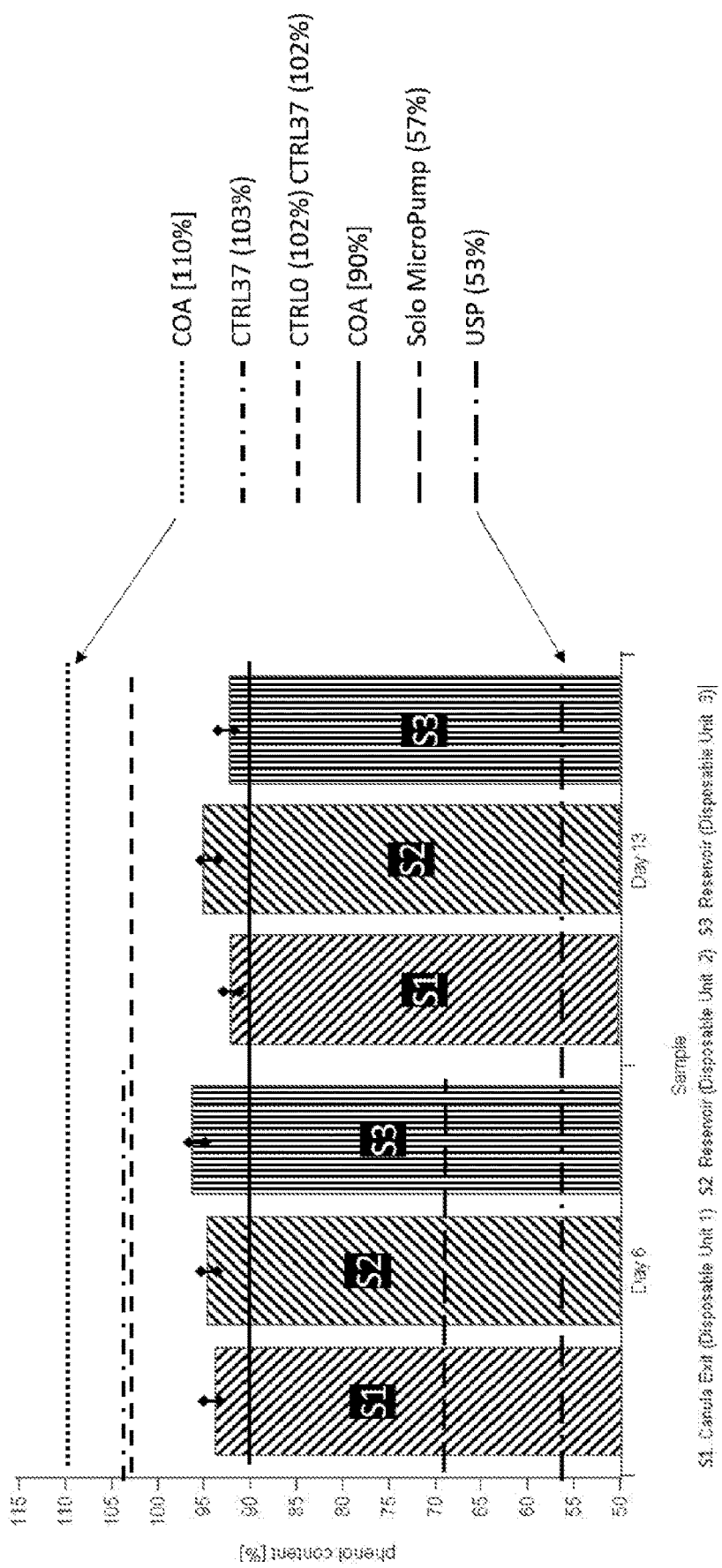
FIG. 7 shows preservative levels of phenol in insulin Aspart.

FIG. 7 shows preservative levels of phenol in insulin Aspart. The results for three Diposable Unit samples are presented as relative percentages to a standard solution; the error bar is RSD (1.1%) of the HPLC analysis. The COA lines are the limit acceptance criteria (90-110%), anotherline is the Control Tat 5° C. (CTRL0 bulk solutions of the insulin vial) and another line is Control T at 37° C. (CTRL37 bulk solutions of the insulin vial) where insulin was exposed to thermal stresses in its original packaging. The "Solo Micropump" dashed line represents the m-cresol level at the Solo MicroPump exit after 6 days of incubation in similar experimental condition and the "USP" dash lines represent the m-cresol effectiveness level according to USP standard.

Figure 8:
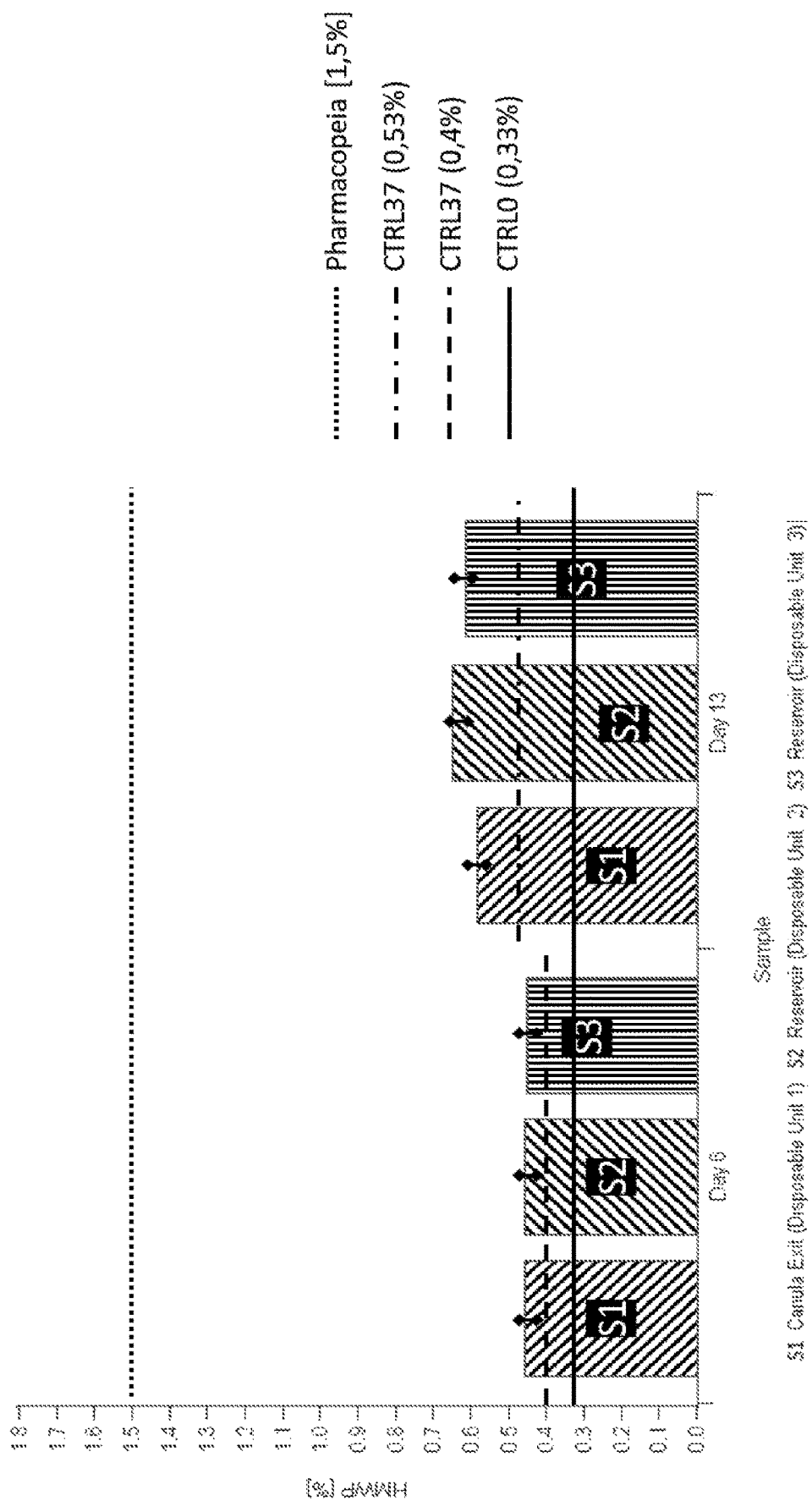
FIG. 8 represents high molecular weight protein levels of Aspart.

High molecular weight protein values were maintained below the 1.50% threshold during 13 days FIG. 8 represents high molecular weight protein levels of Aspart. The results for three Disposable Unit samples are presented as relative percentages of the insulin content (100%). The "Pharmacopeia" line is the limit acceptance criteria (1.5%), another line is the Control T at 5° C. (CTRL0 bulk solutions of the insulin vial) and another line is Control T at 37° C. (CTRL37 bulk solutions of the insulin vial) where insulin was exposed to thermal stresses in its original packaging.

Related substances were maintained below threshold during the 13-day test in all delivered samples.

Figure 9:
FIG. 9 shows B3Asp+A21Asp+B3isoAsp related compounds levels of Aspart.

FIG. 9 shows B3Asp+A21 Asp+B3isoAsp related compounds levels of Aspart. The results for three pump samples are presented as relative percentages of the insulin content (100%). The "Pharmacopeia" line is the limit acceptance criteria (5%), another line is the Control T at 5° C. (CTRL0 bulk solutions of the insulin vial) and another line is Control T at 37° C. (CTRL37 bulk solutions of the insulin vial) where insulin was exposed to thermal stresses in its original packaging.

Figure 10:
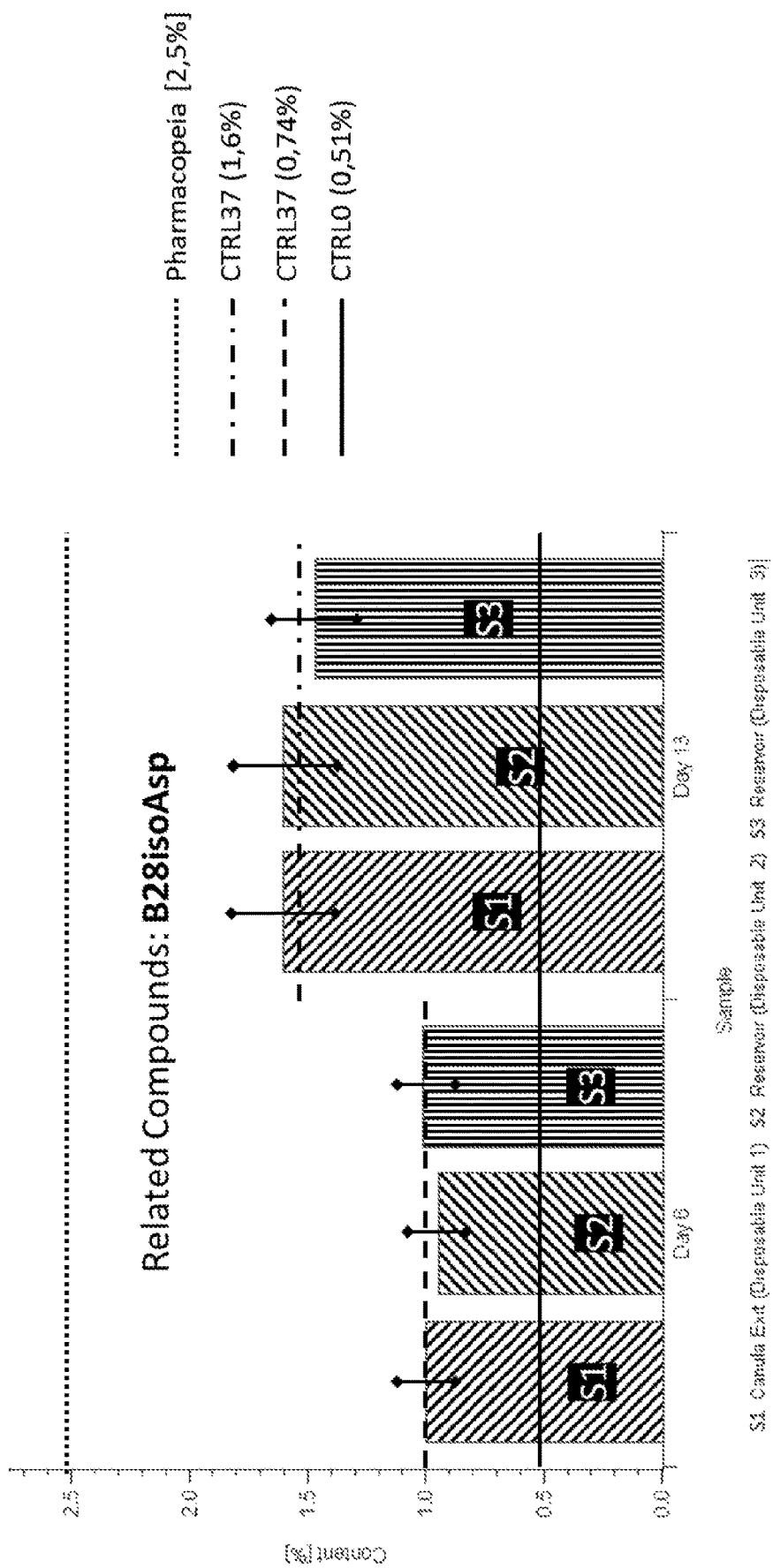
FIG. 10 shows B28isoAsp related compound level of Aspart.

FIG. 10 shows B28isoAsp related compound level of Aspart. The results for three Disposable Unit samples are presented as relative percentages of the insulin content (100%). The "Pharmacopeia" lines is the limit acceptance criteria (2.5%), another line is the Control T at 5° C. (CTRL0 bulk solutions of the insulin vial) and another line is Control T at 37° C. (CTRL37 bulk solutions of the insulin vial) where insulin was exposed to thermal stresses in its original packaging No other related substances were detected after 13 days in the solution and pH after 6 days of incubation was 7.73.

The current study showed 13-day compatibility at extreme conditions for Aspart, with the container disclosed in this document. These results are in agreement with previous studies that demonstrated the compatibility of insulin analog insulin such as Aspart with "pager-like" CSII devices for extended use periods.

MVTR and Thickness

Figure 11:
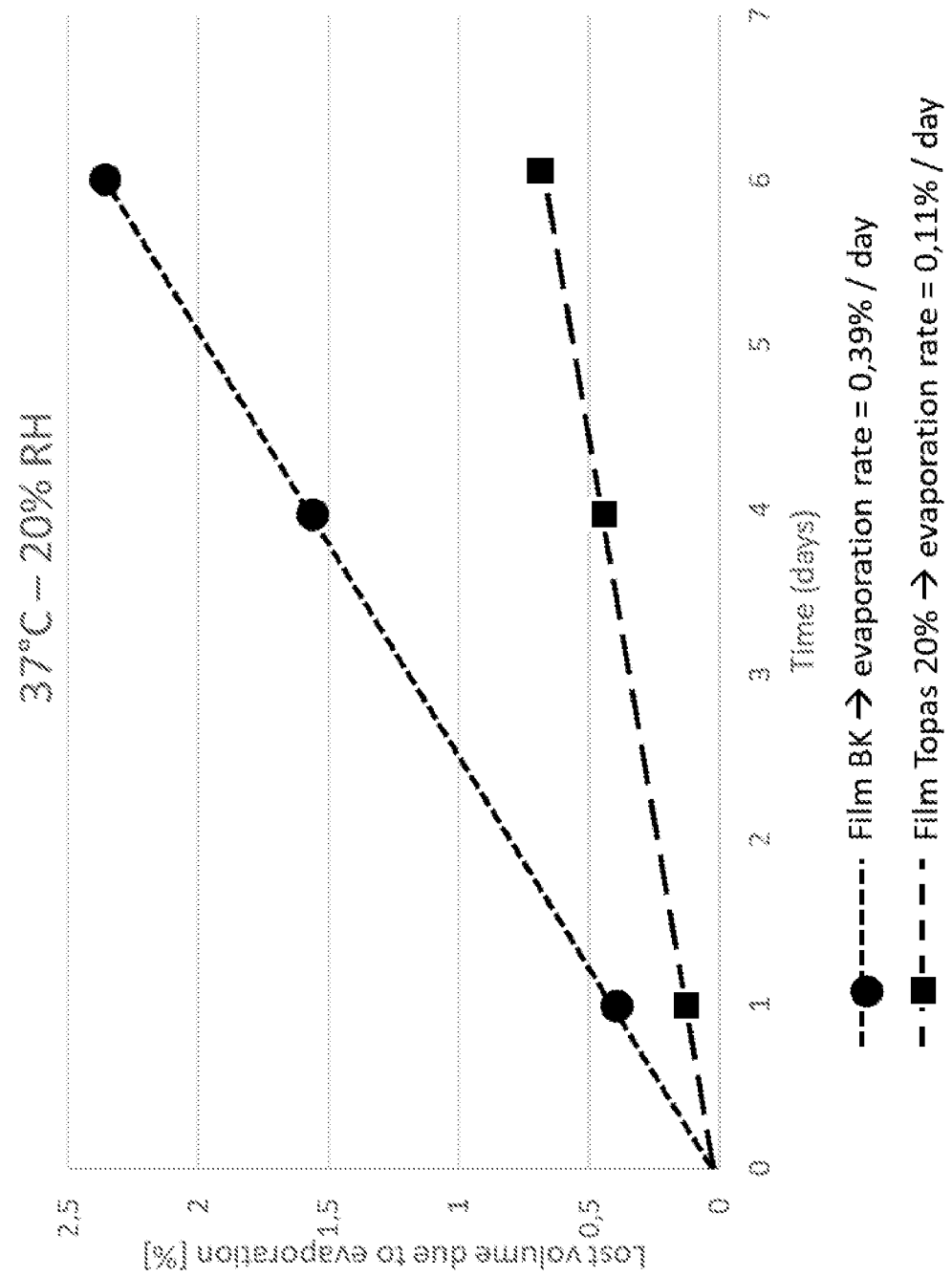
FIG. 11 represents the evaporation monitoring for different film having the same thickness and mounted in the hard shell.

Comparative study was performed between tri-layer film (BK) and single layer COC film mounted on the same hard shell to demonstrate barrier evaporation rate. The relative thickness of the films are 42 um and 51 um, for BK and COC films, respectively FIG. 11 represents the evaporation monitoring for different film having the same thickness and mounted in the hard shell.

COC film demonstrates with a similar thickness than the tri-layer film a better evaporation barrier. This ensures to maintain the integrity of the drug solution as presented in Table 1.

Mechanical Properties Enabling Flexibility and Collapsibility.

The film and its bonding onto the hard shell shall be made such as to resist to a possible overpressure due to an overfilling of the container. Moreover the part of elastomeric polymer added in the flexible film should sufficiently low to not induce any residual elastic strength in the container during the normal use.

Figure 12:
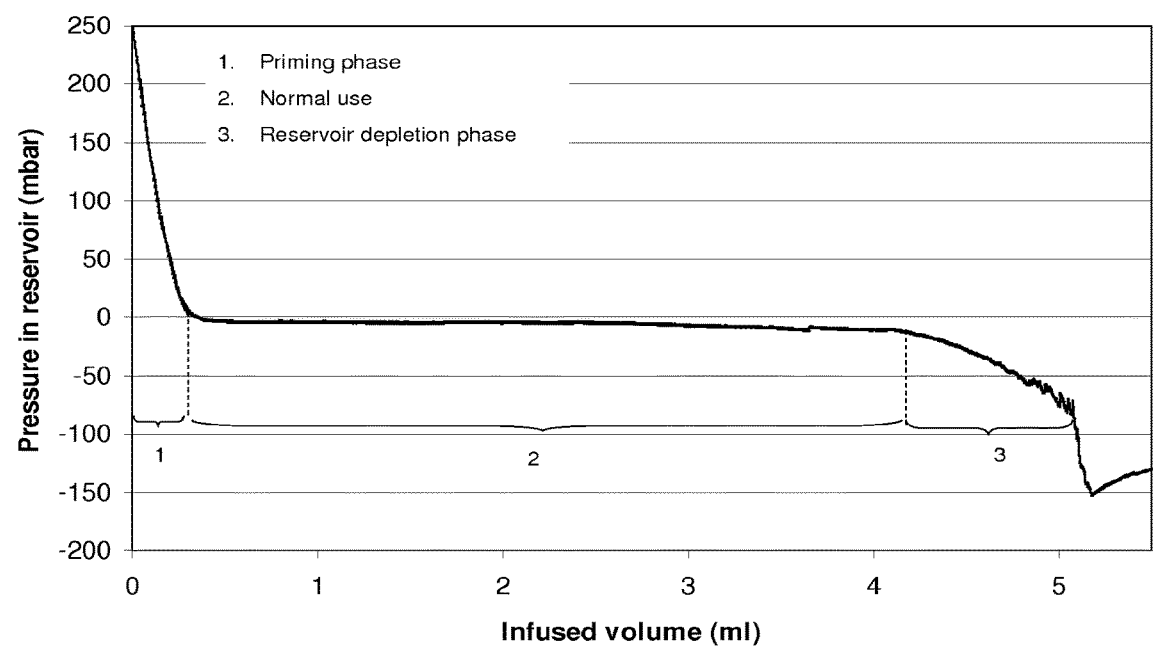
FIG. 12 shows the pressure in the container according to the infused volume.

FIG. 12 shows the pressure in the container according to the infused volume.

Delivery system can be sensitive to elevated over and under-pressures in the container (risk of over infusion in the first case and blockage of the Pump in the second case), the film shall be made so as to avoid large pressure variation due to its deformation during the container emptying (phase 1).

Moreover, the container membrane may ensure the null or slightly negative pressure in the container during the normal use of the pump (phase 2).

During the container depletion (phase 3), the softness of the film ensures a slow decrease of the pressure. This makes possible to have a large reserve volume between the time at which the depletion alarm is triggered and the time at which the pump cannot effectively infuse more liquid.

In a preferred embodiment, the flexible film (1) may exert a pressure within the of +/−20 mbar during the steady state regime. (Note: by steady state regime we understand the so-called "normal use" of FIG. 12, i.e. the period after the priming phase—where the amount of liquid in the container is superior to the nominal value of said container—and the depletion phase—where some parts of the film are in contact with the hard shell of the container.)

Sterilisable and Biocompatible

The use of plastics in the pharma and diagnostics sector in many cases requires sterilizability of the plastic material. The effect of various sterilization methods, using high energy radiation (gamma and electron beam), ETO, hot air and hot steam, has been investigated for Topas. Standard test specimens were subjected to conditions simulating one time exposure. Topas should not be used in applications requiring more than one or two sterilization cycles. Topas COC test specimens maintain mechanical properties after exposure to gamma radiation doses of 50 kGy. Like many other plastics, Topas COC shows a dose-dependent discoloration after exposure to gamma radiation. Grades with improved color stability in gamma irradiation can be requested.

Criteria for the use of plastics in the pharma and diagnostics sector are specified in the national pharmacopoeias (US, EU and JP), and by the appropriate regulatory agencies. Material test program guidelines are given by the FDA, and the International Organization for Standardization (ISO 10993). The test program depends on the particular application and the duration of contact with the human body. Topas COC material biocompatibility testing was carried out according to guidelines given in the FDA Blue Book Memorandum, and by the International Organization for Standardization (ISO 10993). A range of Topas grades were subjected to this material biocompatibility test program. The protocol included the following: Acute Systemic and Intracutaneous Toxicity, Muscle Implantation, Physico-Chemical tests, Blood Compatibility (Hemolysis), and Cytotoxicity. These grades meet the specification of US Pharmacopoeia XXIII—Class VI. Corresponding certificates for specific grades are available. Chemical characterization and extraction tests have been carried out successfully according to the protocols described in the US, EU and Japanese Pharmacopoeia. These tests are intended as a general screening of the materials. The information discussed here should only be used as a starting point for the package/device manufacturer's consideration of the protocol to be used for testing specifically to the particular application. The presentation of these results is thus not intended to replace the testing required of the manufacturer of the package or device. Nor should it be considered a recommendation of the material for any particular application. It is the package/device manufacturer's responsibility to ensure that the materials used for a particular application are suitable for the intended use.

Non Leachable or Substantially Non Leachable

The container should demonstrate acceptable extractables results, under aggressive conditions. In principle, all organic and inorganic compounds eluting under forced conditions have to be monitored. In practice, compounds detection is limited to a concentration above the Analytical Evaluation Threshold.

ICP-MS Results

The analyses of the extractable per ICP-MS through the pump chip have shown the following results: The extraction has presented for the following elements a significant amount of compounds resulting from the pump chip extraction for
Bore in a concentration range of 500-1300 µg/L
Sodium in a concentration range of 100-1100 µg/L
Calcium in a concentration range of 16-20 µg/L
All these elements are not known to have toxic effect; however these results shall be reviewed by a toxicologist for a safety assessment GC-MS Results The results of this analysis of semi-volatile compounds are presented here. The only peak resulting from the test item which was not also present in the Placebo which was used as a control (not contacting the container material) was tentatively identified phthalate with single nitrogen. However, semi quantitative analysis of this peak indicates that the compound is present in range between 0.1 and 0.2 mg/L. By taking a safety factor of 10, this amount remains in the limit threshold for genotoxic elements.

Results from this extraction study suggest that even using exaggerated extraction conditions, the material of the container does release limited amount of compounds and therefore substantially non leachable.

Weld Capable

Various welding methods, except for high-frequency welding, can be used to join molded parts made from Topas COC resin. The most suitable welding method will depend primarily on the specific part.

The invention claimed is:

1. A device for storage of a drug, the device comprising:
a hard shell made of a first material; and
a flexible film bonded to the hard shell defining a liquid-tight container between the flexible film and the hard shell, the flexible film comprising a blend of the first material and a second material, the second material being an elastomeric formulation of the first material such that the hard shell and the flexible film comprise the same first material,
wherein the liquid-tight container is configured to be filled with a liquid pharmaceutical solution,
wherein the flexible film is configured to expand upon filling with the liquid pharmaceutical solution, the flexible film being configured to collapse upon depletion of the liquid pharmaceutical solution, the flexible film being configured to reach a pre-formed shape in which an inner surface of the flexible film closely fits an inner surface of the hard shell upon emptying of the liquid-tight container, and
wherein the collapsing of the flexible film by virtue of the pre-formed shape is not caused by an external force that is applied to the flexible film.

2. The device according to claim 1, wherein the hard shell is made of a single layer.

3. The device according to claim 1, wherein the first material includes a cyclic olefin copolymer (CoC).

4. The device according to claim 1, wherein the flexible film is thermoformed and shaped to closely fit the shape of the hard shell.

5. The device according to claim 1, wherein the container is transparent.

6. The device according to claim 1, wherein the flexible film is enclosed into an additional hard shell, the additional hard shell having openings to guarantee pressure equilibrium between an inside of the additional hard shell and an outside environment.

7. The device according to claim 1, wherein the container is connected to a pump configured to infuse a content of the container into a patient.

8. The device according to claim 1, wherein the flexible film and the hard shell are welded to each other.

9. The device according to claim 1, wherein the liquid pharmaceutical solution includes an active ingredient and at least one preservative selected from the group consisting of phenol and m-cresol.

10. The device according to claim 1, wherein the liquid pharmaceutical solution includes insulin.

11. The device according to claim 1, wherein a thickness of the flexible film is above about 5 μm and is below about 100 μm.

12. The device according to claim 1, further comprising:
an outlet port protected by a filter that is connected to a fluid delivery device to prevent entrapment of air bubbles.

13. The device according to claim 12, wherein the filter is disposed on the hard shell to cover the outlet port.

14. The device according to claim 1, wherein the first material includes rigid polymeric material.

15. The device according to claim 1, wherein the first material is a non-elastomeric material.

16. The device according to claim 1, wherein the flexible film exerts a pressure to an interior of the liquid-tight container within +/−20 mbar during a steady state.

17. The device according to claim 1, wherein the flexible film is configured to expand and collapse to provide for a deformation of the liquid-tight container.

18. The device according to claim 1, wherein the liquid-tight container is defined by a peripheral edge of the hard shell that is connected to a peripheral edge of the flexible film.

19. The device according to claim 1, further comprising:
a sealed inlet configured to permit filling of the liquid-tight container by a fluid transfer device.

20. The device according to claim 19, wherein the sealed inlet includes a septum.

21. The device according to claim 1, wherein the flexible film has a concave shape.

22. A medical device comprising
the storage device according to claim 1; and
a pump.

23. The medical device according to claim 22, wherein the hard shell is interfaced with the pump.

24. A device for storage of a drug, the device comprising:

a hard shell comprising a first material;
a flexible film bonded to the hard shell defining a liquid-tight container between the flexible film and the hard shell configured to be filled with a liquid pharmaceutical solution, the flexible film comprising a blend comprising an elastomeric formulation of the first material such that the hard shell and the flexible film comprise the same first material;
an outlet port connected to a fluid delivery device; and
a filter disposed inside the liquid-tight container on an inner surface of the hard shell to cover the outlet port and configured to prevent entrapment of air bubbles downstream of the outlet port,
wherein the flexible film and the filter are configured so that, when the liquid-tight container is emptied, an inner surface of the flexible film reaches and closely fits the inner surface of the hard shell without needing an external force to the flexible film.

25. A medical device comprising: a drug storage device comprising:
a hard shell comprising a first material,
a flexible film bonded to the hard shell defining a liquid-tight container between the flexible film and the hard shell, the flexible film including a blend of the first material with an elastomer such that the hard shell and the flexible film comprise the same first material, the liquid-tight container being configured to be filled with a liquid pharmaceutical solution, the flexible film being configured to expand upon filling with the liquid pharmaceutical solution, the flexible film being configured to collapse upon depletion of the liquid pharmaceutial solution, the flexible film being configured to reach a pre-formed shape in which an inner surgace of the flexible film closely fits an inner surface of the hard shell upon emptying of the liquid-tight container,
wherein the collapsing of the flexible film by virute of th epre-formed shape is not caused by an external force that is applied to the flexible film.

* * * * *